United States Patent [19]
Lin et al.

[11] Patent Number: 6,041,794
[45] Date of Patent: Mar. 28, 2000

[54] CONNECTOR WITHOUT OCCLUSION

[75] Inventors: Szu-Min Lin, Laguna Hills; Paul T. Jacobs, Trabuco Canyon, both of Calif.; Paul Leonard, Kirkland, Wash.; Rodrigo Berho, Seattle, Wash.; Douglas W. Fett, Lake Stevens, Wash.; Keith Schubert, Redmond, Wash.

[73] Assignee: Ethicon, Inc., Somerville, N.J.

[21] Appl. No.: 09/121,440

[22] Filed: Jul. 23, 1998

[51] Int. Cl.[7] ....................................... B08B 9/00
[52] U.S. Cl. .................... 134/22.11; 134/22.12; 134/166 C; 134/169 C
[58] Field of Search ............. 134/22.12, 22.11, 134/22.18, 21, 42, 166 C, 169 C; 137/240

[56] References Cited

U.S. PATENT DOCUMENTS

| | | | |
|---|---|---|---|
| 4,526,622 | 7/1985 | Takamura et al. | 134/21 |
| 4,526,623 | 7/1985 | Ishii et al. | 134/21 |
| 4,576,650 | 3/1986 | Yabe et al. | 134/22.12 |
| 4,579,597 | 4/1986 | Sasa et al. | 134/21 |
| 4,579,598 | 4/1986 | Sasa et al. | 134/22.12 |
| 4,637,378 | 1/1987 | Sasa | 128/4 |
| 5,755,894 | 5/1998 | Bowman et al. | 134/22.12 |
| 5,795,403 | 8/1998 | Biermaier | 134/22.12 |
| 5,795,404 | 8/1998 | Murphy et al. | 134/22.12 |
| 5,803,101 | 9/1998 | Gallo | 134/166 C |
| 5,827,744 | 10/1998 | Fose et al. | 134/22.11 |

*Primary Examiner*—Randy Gulakowski
*Assistant Examiner*—Saeed Chaudhry
*Attorney, Agent, or Firm*—Knobbe, Martens, Olson & Bear, LLP

[57] ABSTRACT

A connector for use with a lumen device during the cleaning and sterilization of devices is provided. The connector provides fluid communication between a fluid source and the device. In particular, during the cleaning and sterilization cycle, the connection between the connector and the device does not produce occluded areas at the point of connection where the connector is sealably attached to the device.

10 Claims, 10 Drawing Sheets

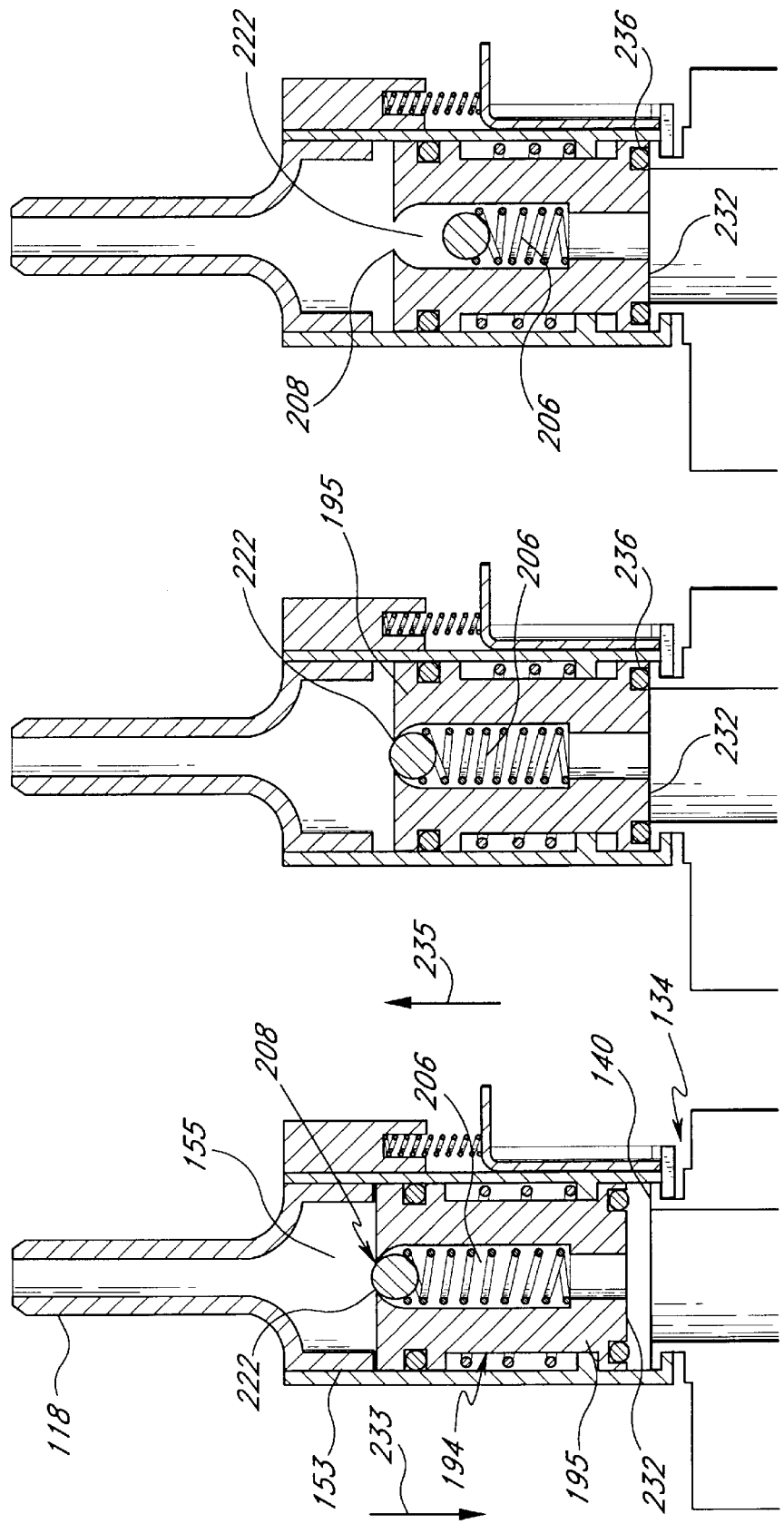

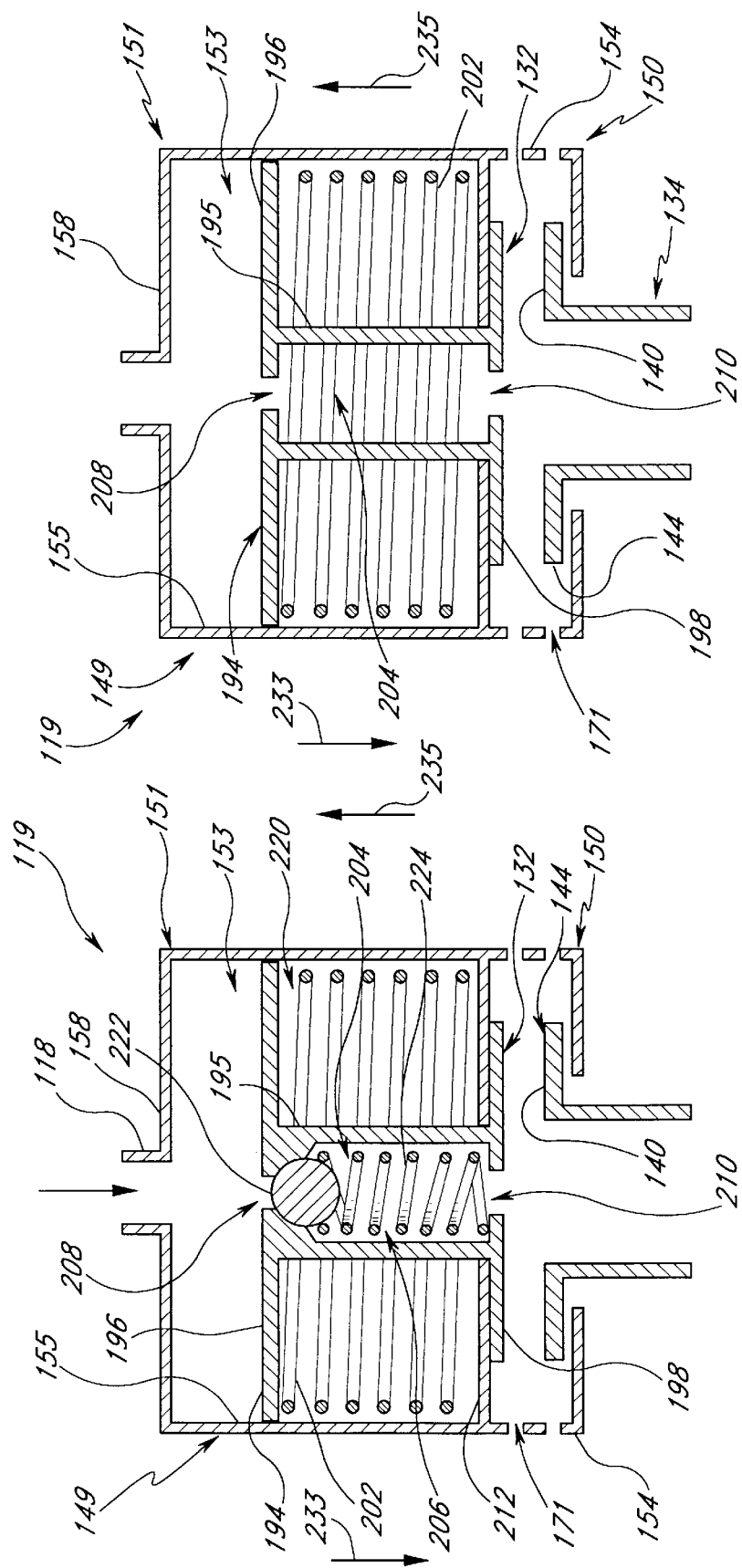

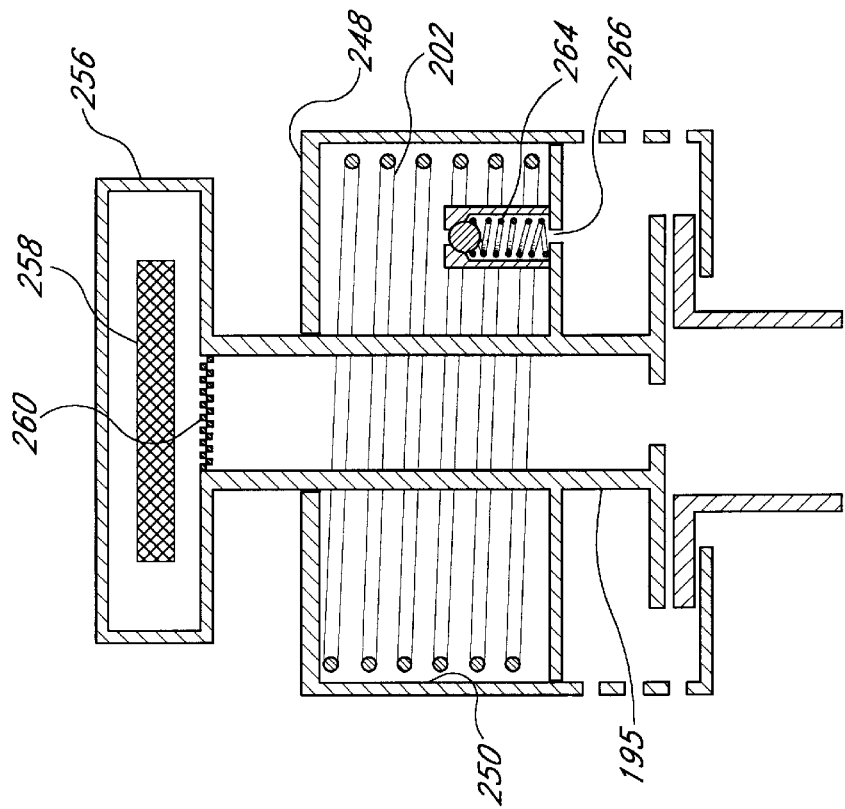
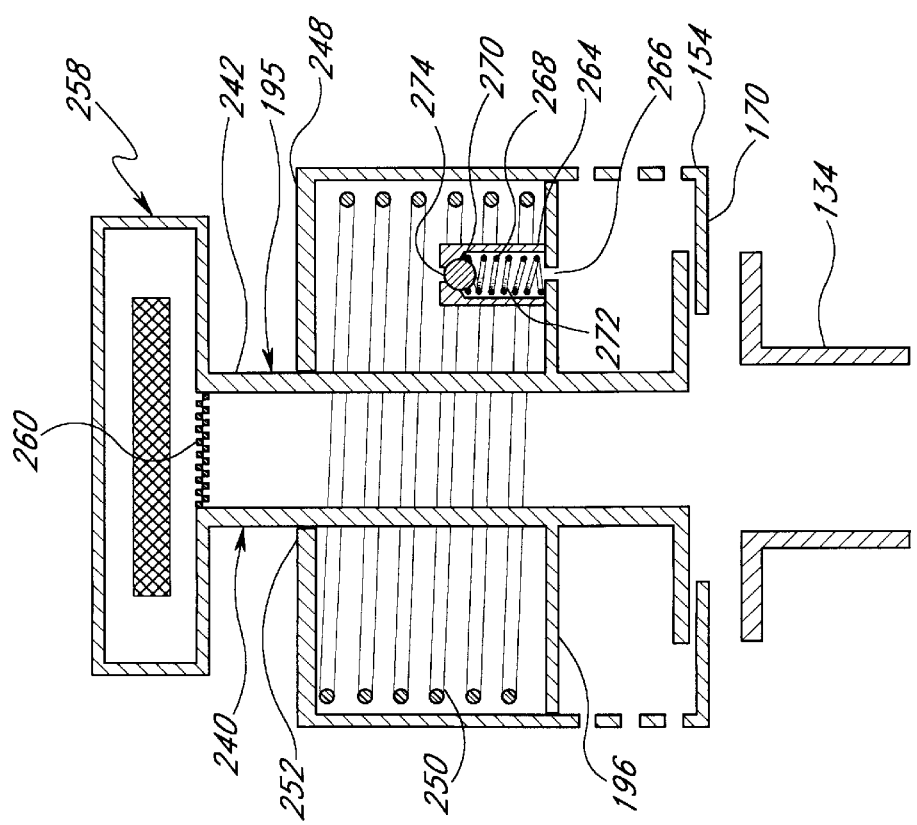
FIG. 11
FIG. 10

CONNECTOR WITHOUT OCCLUSION

BACKGROUND OF THE INVENTION

1. Field of the Invention

This invention generally relates to a system and method for cleaning and sterilizing lumen devices and, more particularly, to techniques for cleaning and sterilizing the interior of the lumen devices and connection points.

2. Description of the Related Art

In modern medical practices, it has been a common practice to sterilize medical or surgical instruments used for medical or surgical purposes before each use. It is important that the cleaning and sterilization of such instruments be performed efficiently and quickly without leaving potential occluded areas in the instruments. However, the ever increasing complexity of such instruments requires corresponding modifications in conventional cleaning and sterilization techniques and processes, which makes the cleaning and sterilization related problems one of the critical aspects of such instruments.

This is of particular relevance to the instruments comprising elongated channels, such as endoscopes. A typical endoscope generally includes an elongated tubular body having a distal portion and a proximal portion. The distal portion of the endoscope is generally flexible enough to be inserted into a human or animal body so that a lens at the distal end provides an image of an internal area of the body. An image transmission means, such as fiber optic cables, transmits the image of that location from the distal tip, through the proximal portion, to a point outside of the body where it can be viewed by a surgeon or other user of the endoscope. In addition to the image transmission means, the body of the endoscope generally contains one or more channels having at least two open ends along the endoscope body. These channels define a fluid flow path suitable for passing fluids or possibly introducing instruments into a human body. After each use, it is important that these channels, along with the external surfaces of the endoscope, be carefully washed and sterilized for reasons of sanitation.

In one conventional process, cleaning and sterilization of the channels can be provided by flowing a fluid, such as a cleaning solution, a disinfectant or a sterilant, through these channels. In such processes, one opening of a channel may be connected to a fluid delivery source to facilitate the delivery of the fluid into the channel thereby flowing the fluid through the channel to wash, disinfect and/or sterilize the channel.

In general, a connection between the channel openings and the fluid source is provided through a connector. The connector is attached sealably to one or more channel openings so as to allow fluid communication between the channel and the fluid source. Although this process efficiently treats the channels with a fluid, connection between the connector and the lumen device produces occluded areas at the point of connection where the connector is sealably attached to the lumen device. Thus, since these areas are masked by the connector, the fluid flowing into the channel cannot clean and sterilize the connection surfaces.

Thus, there is a need for a cleaning and/or sterilization process having a connector which can deliver fluid to the interior of lumen devices without creating occluded areas around the connection surfaces.

SUMMARY OF THE INVENTION

The aforementioned needs are satisfied by the system of the present embodiment which allows the operator to perform multiple cleaning and sterilization sequences without interrupting the cycle. Specifically, the connector of this embodiment entirely automates the cleaning and sterilization system and provides the benefit of not leaving any occluded area between the connector and the lumen device.

It will be appreciated that there are multiple aspects of the present invention. In one aspect of the present invention, a connector for use with a lumen device that provides fluid communication between a fluid source and the lumen device is provided. The connector is configured to engage with a port on the lumen device wherein the port includes a sealing surface. The term "pressure actuated" as defined in this application is not limited to members actuated by pressure alone but also encompasses actuation with a solenoid, electromagnet, or a pneumatic device. The connector includes a housing defining a space, a pressure actuated member positioned within the space so as to be movable therein, a piston surface formed on the pressure actuated member that engages with the sealing surface of the port of the lumen device. The pressure actuated member defines at least one passageway for the fluid to flow from the fluid source to the lumen device through the connector. Further, the piston surface is less than fully engaged with the sealing surface when the pressure actuated member is in a first position. However, the piston surface fully engages with the sealing surface when the pressure actuated member is in a second position allowing the fluid enter the lumen device.

In another aspect of the present invention, a method for cleaning or sterilizing interior and exterior of a lumen device is provided. The lumen device has a port that is connected to the interior of the lumen device, and the port has a sealing surface. The method includes the following steps. In the first step, a connector device is connected to the port. The connector has a housing and a pressure actuated member which is movably positioned within said housing. Further, the pressure actuated member defines a passageway to allow fluid flow through the connector. In the second step, the connector device and the lumen device are placed in a chamber. However, the first and second steps can be performed in any order. In the third step, the pressure actuated member positioned in a first position in which the connector is connected to the port and the lumen device is subjected to a fluid so that the fluid contacts the sealing surface of the port, and thereby treating the sealing surface with the fluid. In the fourth step, the pressure actuated member is positioned in a second position. When the pressure actuated member is in the second position, a piston surface of the pressure actuated member fully engages with the sealing surface so as to induce the piston surface to seal with the sealing surface thereby allowing the fluid flowing into the interior of the lumen device. The step of positioning the pressure actuated member in a first position and the step of positioning the pressure actuated member in a second position can be performed in either order.

In another aspect of the present invention, a connector for use with a lumen device that provides a sterilization fluid to the lumen device in a sterilization environment is provided. The connector is configured to engage with a port on the lumen device and the port includes a sealing surface. The connector includes a housing that is adapted to receive the port and defines a space, a sterilant enclosure containing a sterilization fluid connected to the space, a pressure actuated member positioned within said space so as to be movable therein, a piston surface formed on the pressure actuated member that engages with the sealing surface of the port of the lumen device. The pressure actuated member defines at least one passageway for sterilization fluid to flow from the sterilant enclosure to the lumen device. Further, the piston surface is less than fully engaged with the sealing surface when the pressure actuated member is in a first position. Moreover, the piston surface fully engages with the sealing surface when the pressure actuated member is in a second position allowing the sterilization fluid from the enclosure enter the lumen device.

In yet another aspect of the present invention, a method for sterilizing interior and exterior of a lumen device is provided. The lumen device has a port that is connected to the interior of the lumen device. Further, the port has a sealing surface. The method includes the following steps. In the first step, a connector device is connected to the port, and to a source of sterilant. The connector device has a housing and a pressure actuated member is movably positioned within the housing. The pressure actuated member defines a passageway to allow sterilant flow through the connector. In the second step, the connector device and the lumen device are placed in a sterilization chamber. However, the first and second steps can be performed in any order. In the third step, the pressure actuated member is positioned in a first position in which the connector is connected to the port and the lumen device is subjected to a sterilant so that the sterilant contacts the sealing surface of the port thereby treating the sealing surface with the sterilant. In the fourth step, the lumen device is subjected to reduced pressure. Finally, in the fifth step, the pressure actuated member is positioned in a second position. When said pressure actuated member is in the second position, a sterilant flows through the path way and a piston surface of the pressure actuated member fully engages with the sealing surface so as to induce the piston surface to seal with the sealing surface thereby allowing the sterilization fluid flowing through the path way to enter the interior of the lumen device. The step of positioning the pressure actuated member in a first position, the step of subjecting the lumen device to reduced pressure and the step of positioning the pressure actuated member in a second position can be performed in any order.

These and other objects and advantages of the present invention will become more fully apparent from the following description taken into conjunction with the accompanying drawings.

BRIEF DESCRIPTION OF THE DRAWINGS

FIGS. 5A–5C are cross-sectional views of the connector of FIG. 3A, showing operation of the connector; and FIGS. 6–15 are cross-sectional graphical views of the various embodiments of the connector of this invention.

DETAILED DESCRIPTION OF THE PREFERRED EMBODIMENT

Figure 1A:
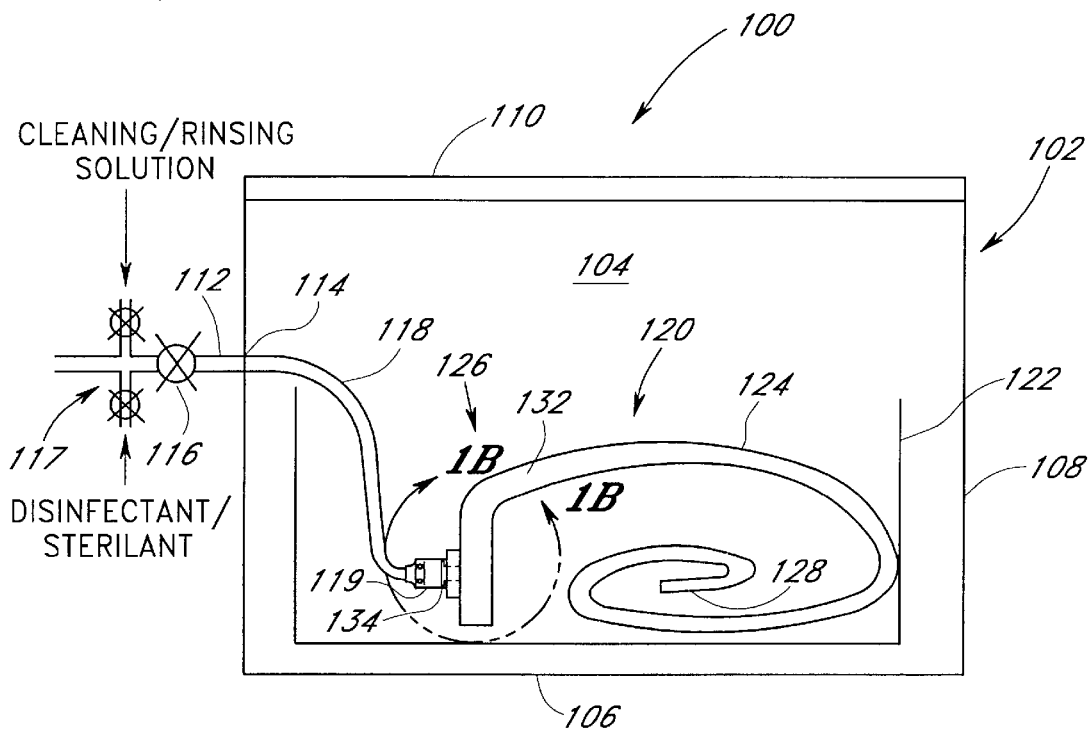
FIG. 1A is a schematic view of an embodiment of a cleaning/sterilization system comprising an endoscope which is connected to the system.

Reference will now be made to the drawings wherein like numerals refer to like parts throughout. FIG. 1A shows a system 100 for cleaning and sterilization of lumen devices, such as endoscopes. The system 100 comprises a chamber 102 having an inner chamber 104 for containment of the articles being processed, i.e., either cleaned or sterilized. The inner chamber 104 is enclosed by a chamber floor 106, a peripheral wall 108 and a lid 110. An external fluid flow pipe 112 connects a fluid source (not shown), such as a cleaning solution, a liquid disinfectant or a liquid sterilant, to an opening 114 on the chamber 102. An external valve 116 may be provided to open and close the fluid flow path between the fluid source and the chamber 102. Optionally, an external connector 117 may connect the valve 116 to more than one fluid source or a vacuum source (not shown) as in the manner shown in FIG. 1A. In the inner chamber 104, an internal fluid flow pipe 118 connects the opening 114 to a connector 119, preferably a pressure sensitive connector. As exemplified in FIG. 1A, the connector 119 may be connected to an endoscope 120 to deliver desired fluids for cleaning and sterilization to the endoscope 120.

As illustrated in FIG. 1A, the endoscope device 120 may be placed into the inner chamber 104 in an optional tray 122. The endoscope 120 comprises an elongated tubular body 124 having a proximal end 126 and a distal end 128. As described previously, an endoscope may have more than one channel to deliver or collect fluids from various body locations. However, it will be appreciated that the number of channels or their configuration is not pertinent to the present invention. As shown in detail in FIG. 1B, the proximal end 126 of the endoscope may comprise a port 134 formed on a base block 135 of the port 134 and connected to a channel(s) (not shown) within the endoscope 120 via a port cavity 136. The port cavity 136 connects the endoscope channel (not shown) to an aperture 137 defined at the center of the port 134. The block 135 is attached to the proximal end 126 of the endoscope 120.

Figure 2A:
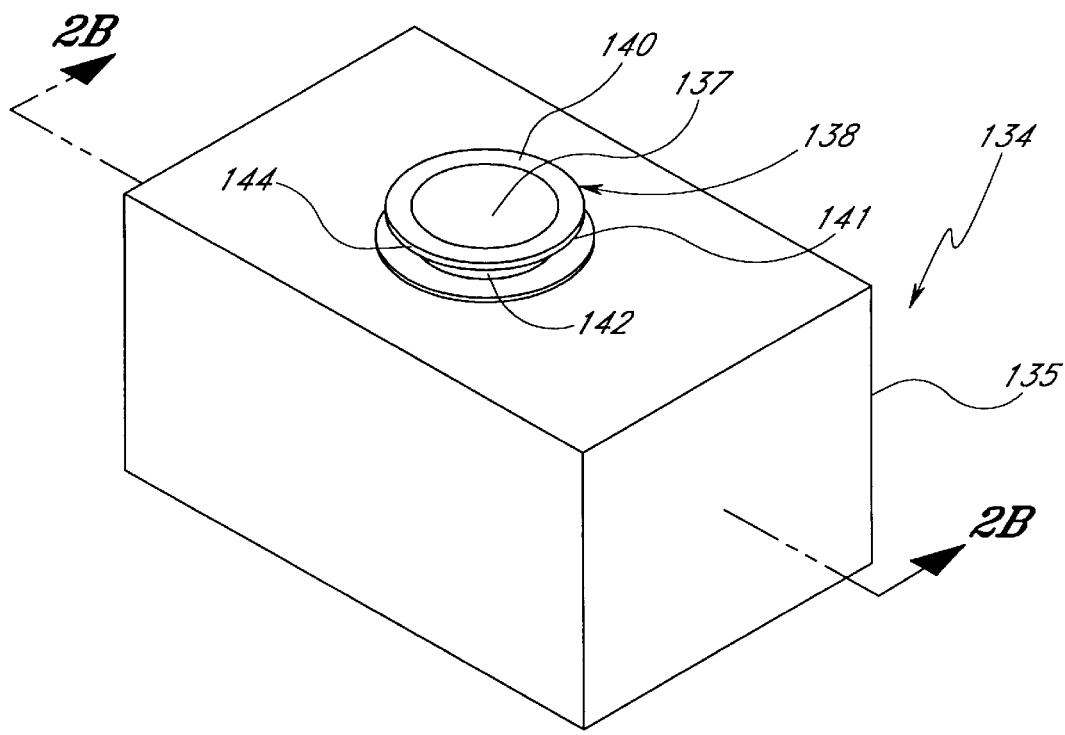
FIG. 2A is a perspective view of a port of the endoscope.
Figure 2B:
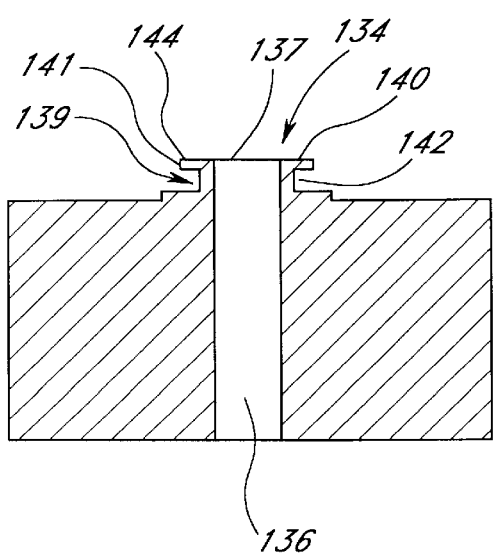
FIG. 2B is a cross-sectional view of the port of the endoscope taken along the line 2B—2B of FIG. 2A.

As shown in FIGS. 2A–2B, the port 134 is generally adapted to have a circular lip portion 138 and a circumferential track 139 formed beneath the lip portion 138. The circular lip portion 138 extends radially outward from the perimeter of the aperture 137 and defines a sealing surface 140 and a side surface 141. The circumferential track 139 is preferably configured to have a rectangular "C" shape and defines a track surface 142. In this embodiment, for the sake of simplicity, the surfaces 140, 141 and 142 of the port 134 will be referred to hereafter as the outer surface 144 of the port 134. As will be explained more fully below, connecting the endoscope 120 to the connector 119 may produce occluded areas at the outer surface 144 of the port 134. In other words, a portion of the surfaces 140, 141 and 142 is masked by the connector because the fluid flowing into the channel cannot clean and sterilize these surfaces 140, 141 and 142.

Figure 3A:
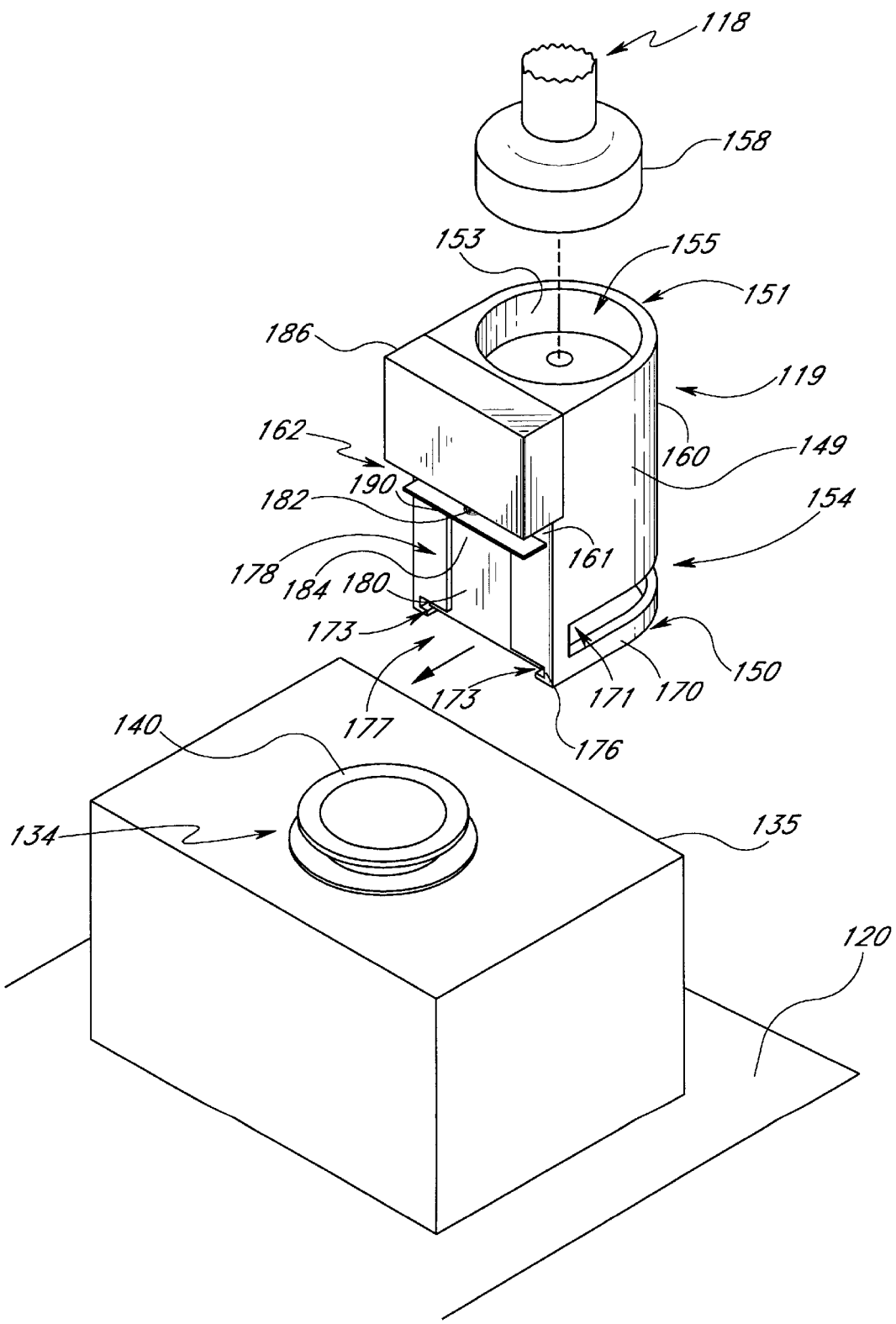
FIG. 3A is an exploded perspective view showing the connector in actual alignment in position for the connection with the port of the endoscope.

The connector device 119 of the present invention will now be described in reference to FIGS. 3A–5C. Referring to FIG. 3A, a longitudinal sectional exploded view shows the connector 119 in actual alignment for connection with the port 134 of the endoscope 120. As will be described more fully below, the connector device 119 allows a fluid to flow into the endoscope 120 without creating occluded areas on the outer surface 144 of the port 134. The connector 119 comprises a housing 149 comprising a lower end 150, an upper end 151, and a central bore 153. The lower end 150 of the housing 149 may comprise a connection compartment 154 to removably connect the connector 119 to the port 134 of the endoscope 120. An upper section 155 of the central bore 153 may be connected to a tubing connector 158 which connects the connector 119 to the inner conduit 118. As will be explained more fully below, the central bore is adapted to have a piston assembly 194 which is fitted along the central bore 153 (See FIG. 4). Thus, a lower section 156 of the central bore may have a locator ring 212 which supports and centers the piston assembly 194 within the central bore.

The housing 149 may comprise a curved wall portion 160 and a flat wall portion 161. The curved wall section 160 is preferably configured to have the "U-shape" in horizontal cross-section. A lock assembly 162 may be positioned on the flat wall portion 161 of the housing 149. In particular, in the preferred embodiment, the connection compartment 154 comprises a connection member 170 which is preferably a U-shaped rail corresponding to the shape of the curved wall 160. Either end of the U-shaped rail 170 of the connection compartment 154 terminates at the flat wall 161 with a pair of horizontal slots 173 having openings 176 facing one another. The connection member 170 may preferably be spaced apart from the curved wall 160 of the housing 149 by a lateral opening 171. As will be described more fully below, the lateral opening 171 allows fluid to flow out of or into the connection compartment 154 so as to treat the outer surface 144 of the port 134.

At this point, it will be understood that the lateral slots 173 define an entrance 177 for the connection compartment 154 so as to slidably receive the circular lip portion 138 of the port 134. In this respect, the connection member 170, inclusive of the horizontal slots 173 and the openings 176, are sized to receive the lip portion 138 of the port 134. As will be explained more fully below, when the circular lip portion 138 of the port 134 is received by the connection compartment 154, the port 134 will be in a loose engagement with the connection member 170. That is, the port 134 may not be held tightly by the connection member 170 of the connection compartment 154. To the contrary, the port 134 may wobble without disengaging from the connection member 170. As will be further explained hereinbelow, in this loosely connected state, the connector 119 allows the fluid from the tray 122 to flow around and clean and sterilize the sealing outer surface 144 of the port 134. Once engaged with the connection member 170 and placed into the connection compartment 154, a lock plate 180 of the lock assembly 162 retains the port 134 in the compartment 154 by blocking the openings 176.

Figure 3B:
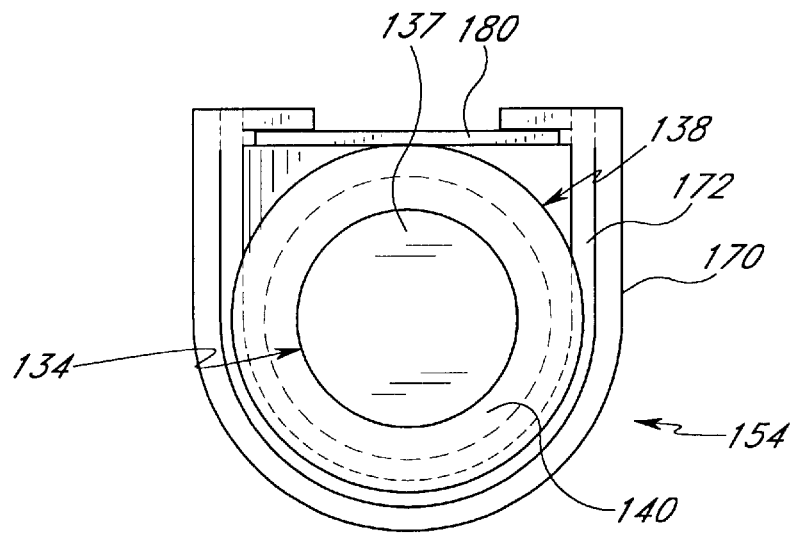
FIG. 3B is a plan cut-out view of the connection compartment, wherein the port of the endoscope is in the connection compartment.

As illustrated in FIGS. 3A–3B, in this embodiment, the lock assembly 162 comprises a lock plate housing 178, the lock plate 180 and a lock spring 182. The lock assembly 162 retains the port 134 in the connection compartment 154. The lock plate housing 178 is comprised of two vertical slots 184 located on both vertical ends of the flat wall 161 of the connector housing 149. The vertical slots 184 extend between the proximity of a spring housing 186 and the proximity of the horizontal slots 176 of the connection compartment 154. The vertical tracks 184 may preferably be formed as an integral part of the connector housing 149 and on vertical edges of the flat wall 161.

The vertical slots 184 are sized and shaped to movably receive the lock plate 180 which is coupled to the lock spring 182 that is positioned in the spring housing 186. The upper end of the lock plate 180 may also comprise a handle 190 extending outwardly perpendicular from the lock plate 180. The lock plate 180 is sized and shaped to close (i.e., to lock) or open the entrance 177 of the connection compartment 154. In this respect, the plate 180 is configured to have a vertical length such that when the plate 180 is spring loaded the lower end of the plate 180 blocks the horizontal slots 176 of the connection compartment 154 thereby closing the entrance 177 of the connection compartment 154. In order to open the entrance 177, the lock plate 180 is moved upward by forcing the handle 190 towards spring housing 186 so as to retract the spring 182 into the spring housing 186 and to bring the lock plate 180 into its open position. Normally, the lock plate 180 is held in a closed disposition.

Figure 4:
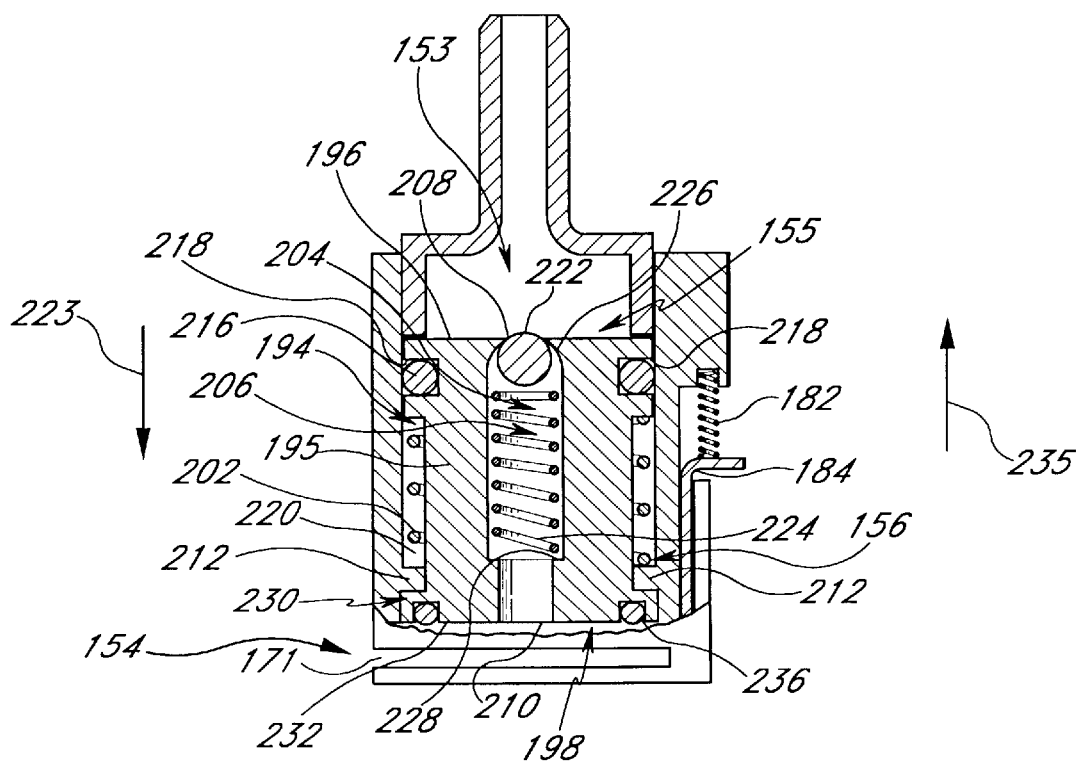
FIG. 4 is a cross-sectional view of the connector.

As already noted above, the port 134 of the endoscope 120 is connected to the connector 119 through the connection compartment 154 and retained in the compartment 154 by the lock plate 180 of the lock assembly 162. A sectional view, as shown in FIG. 3B, illustrates the connection compartment 154 engaged with the port 134 of the endoscope 120 in actual alignment and position. When the port 134 is fully inserted into the connection compartment 154, the circular lip portion 138 of the port 134 rests on a horizontal lip section 172 of the connection member 170. The horizontal lip section 172 extends inside horizontally along the connection member 170. As illustrated in FIG. 4, the connector 119 comprises a piston assembly 194 which is concentrically received within the central bore 153. The piston assembly 194 preferably comprise a piston body 195 with an upper plate 196, a lower plate 198 and an inner bore 204. The inner bore 204 extends along the body 195 and between an upper aperture 208 defined by the upper plate 196 and a lower aperture 210 defined by the lower plate 198. The apertures 208 and 210 are formed at the centers of the plates 196 and 198 respectively. Referring to FIG. 4, the upper plate 196 of the piston body 195 is shaped as a flat disk having a diameter which is slightly smaller than the diameter of the central bore 153. The perimeter of the upper plate 196 is provided with a sealing member 216, preferably an o-ring. The o-ring 216 is nested in an o-ring groove 218 which is a radial groove formed along the perimeter of the upper plate 196 as in the manner shown in FIG. 4. The o-ring 216 forms a fluid tight seal between the edge of the upper plate 196 and the wall of the central bore 153. As previously mentioned, the piston body 195 is centered within the central 153 bore by the locator ring 212 which is appropriately sized to permit the piston body 195 to slip freely through the locator ring 212. The upper plate 196 and the locator ring 212 cooperate to stabilize the axial movement of the piston body 195 through the central bore 153. Additionally the locator ring 212 and the upper plate 196 radially space the piston from the bore 153 thereby defining a coaxial housing 220 to accommodate a biasing element 202. In this embodiment, the biasing element 202 is preferably a coil spring.

Referring to FIG. 4, the lower plate 198 of the piston body 195 is configured as a flange 230 defining a piston surface 232 disposed concentrically radially about the lower aperture 210. The piston surface 232 may be provided with an o-ring 236 which is concentrically fitted on the surface 232 in a manner known in the art. In this embodiment, the piston surface 232 is sized to fit on the sealing surface 140 of the endoscope port 134. At rest, when there is no fluid pressure on the piston, the piston spring 202 urges the lower plate 198 against the locator ring 212 by the spring tension thereby retaining the piston body 195 at this rest state as in the manner shown in FIG. 4. In this embodiment, when the spring 202 is compressed the piston moves in a first direction as depicted by the arrow 233. This compression can be provided by applying a pressure over the upper plate 196 and moving the piston body 195 in the first direction 233. As expected, when the pressure is completely relieved, the piston moves in a second direction 235 until the lower plate 198 rests against the locator ring 212.

Referring to FIG. 4, in this embodiment, the inner bore 204 comprises a valve 206 which is preferably comprised of a ball 222 and a valve spring 224. As will be explained more fully below, the valve 206 allows fluid communication between the fluid source and the endoscope 120 when the fluid pressure in the upper section 155 of the central bore 153 is high enough to dislodge the ball and hence open the valve 206. The upper portion of the inner bore 204 is narrowed towards the upper aperture 208 by a tapered portion 226 where the ball 222 of the valve 206 is received. The diameter of the ball 222 is larger than the diameter of the upper aperture 208. The lower portion of the inner bore 204 is narrowed by a radial seat 228 on which the valve spring rests as in the manner shown in FIG. 4. At rest, the valve spring 224 urges the ball 222 against the upper aperture 208 and provides a secure seal with the upper aperture 208 of the inner bore 204.

Figure 1B:
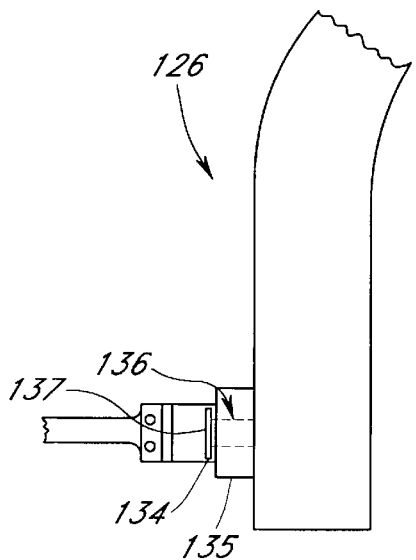
FIG. 1B is a schematic view of a proximal portion of the endoscope shown in FIG. 1A.

The operation of the connector 119 is as follows:

Referring to FIGS. 1A–1B, the endoscope device 120 is placed into the tray 122 in the inner chamber 104 of the chamber 102. According to principles of the present invention, the tray 122 may also comprise some fluid. The connection between the endoscope 120 and the system 100 can be established through the connector 119 of the present embodiment. As discussed above, the connector 119 contains a connection compartment 154 to receive the port 134 of the endoscope 120. The port 134 is admitted into the connection compartment 154 by opening the entrance 177 and sliding the lip portion 138 of the port 134 through the horizontal slots 176 of the connection compartment 154. In order to open the entrance 177 the lock plate 180 is moved against the spring housing 186 of the lock assembly 162. Once the port 134 is placed into the compartment 154, the lock plate 180 is released to close the entrance 177 and to retain the port 134 in the connection compartment 154. Upon connecting the connector 119 to the port 134, the chamber 102 is sealed for the cleaning and sterilization process.

FIG. 5A illustrates the connection between the port 134 and the connector 119 while also showing the relative orientation of the piston surface 232 of the piston body 195 to the sealing surface 140 at an initial fluid pressure. At this initial pressure level, the piston body 195 is in a first position so that the piston surface 232 is not in contact with the sealing surface 140 of the port 134. Further, at this initial pressure, the valve 206 remains in its off state and closes off any fluid flow between the upper portion 155 of the central bore 153 and the connection compartment 154 through the valve housing 204. Thus, the initial pressure is not high enough to move the piston assembly downwards or to displace the ball 222 of the valve 206 from its fluid tight fit against the upper aperture 208 of the inner bore 204. As opposed to prior art connectors, in its loosely connected state, the connector 119 allows fluid from the tray 122 (See FIG. 1A) to flow around and sterilize and clean the outer surface 144 of the port 134. The agitation of the fluid in the chamber enhances the cleaning and sterilization of the areas around the piston surface and the sealing surface. As discussed in the background section, the prior art connectors cause occluded areas at the connection surfaces such as the sealing surface 140, side surface 141 and track surface 142 of the port 134. In the prior art, such occluded areas require another cleaning and sterilization step to treat the occluded areas.

FIG. 5B shows the connector 119 at an intermediate fluid pressure where the piston body 195 is urged into a lower position (in the direction of arrow 233) wherein the o-ring 236 on the piston surface 232 is in contact with the sealing surface 140 of the port 134. In this second position, the sealed state between the o-ring 236 and the sealing surface 140 prevents any fluid flow between the piston surface 232 and the sealing surface 140, thereby occluding the sealing surface 140. As in the previous pressure level, the ball 222 remains seated at the upper aperture 208 of the inner bore 204 and thus prevents any fluid flow into or out of the port 134.

As illustrated in FIG. 5C, the connector 119 is at a high fluid pressure when the piston body 195 is still at the lower position where the o-ring 236 on the piston surface 232 is in contact with the sealing surface 140. However, this increased pressure level opens the valve 206 by overcoming the strength of the spring 224 and then moving the ball 222 downward (in the direction of arrow 233) in the valve housing 204 thereby allowing fluid flow into the endoscope 120. As understood, the movement of the piston body 195 is closely related to the strength of the spring 202, while the action of the valve 206 depends on the strength of the valve spring 224. If the compressive force required to compress the valve spring 224 is less than the compressive force required to compress the spring 202, the valve 206 opens before the piston body 195 is urged into a lower position, and initiates the fluid flow over the occluded areas.

It is to be understood that the pressure activated device described above can include a solenoid or pneumatic device.

The system of the present embodiment allows for the operator to perform cleaning and/or sterilization without creating occluded areas between the connector 119 and the lumen device. It will be understood that the present invention is susceptible to modification in order to adapt it to different uses and conditions. In order to better describe the concept of the alternative embodiments and to clearly indicate the corresponding modifications on the connector 119, the following embodiments will be described with the assistance of simplified illustrations. In this respect, the connector 119 of the present invention, as shown in FIG. 5, will be briefly redescribed using a simplified illustration of the connector 119 shown in FIG. 6.

FIG. 6 shows the connector 119 which is connected to the port 134 of the endoscope 120. As described above, the connector 119 comprises the housing 149 having the lower end 150, the upper end 151 and the central bore 153. The lower end 150 of the housing 149 comprises the connection compartment 154 where the port 134 of the endoscope is received. The lateral openings 171 of the connection compartment 154 allow an outside fluid, such as the solution in the tray 122 (See FIG. 1A), to enter into the connection compartment 154 and contact the outer surface 144 of the port 134. The solution may be a cleaning, rinsing, disinfectant and sterilization solution. The upper end 151 of the housing 149 comprises the tubing connector 158 so that the upper portion 155 of the central bore 153 is connected to the inner conduit 118 which is also connected to the fluid source (not shown).

The central bore 153 comprises the piston assembly 194 which is centered within the central bore 153. The piston assembly 194 comprises the piston body 195 having upper and lower plates 196 and 198, and the piston spring 202, which is concentrically placed around the piston body 195 and in the coaxial spring housing 220. The inner bore 204 comprises the valve 206 and is centrally longitudinally located within the piston body 195. The inner bore 204 extends between the upper aperture 208 located at the upper end 196 of the piston body 195 and the lower aperture 210 located at the lower end 198 of the piston body 195. The inner bore 204 connects the upper portion 155 of the central bore 153 to the connection compartment 154. The valve 206 is positioned within the inner bore 204 and comprises the ball 222 and the valve spring 224. The valve spring 224 urges the ball 222 towards the upper aperture 208 and forms a fluid tight seal therein. The lower end 198 of the piston body comprises a piston surface 132 to sealably contact with the sealing surface 140 of the port 134 when the piston body 195 is moved toward the sealing surface 140 with the increasing fluid pressure as in the manner described above.

FIG. 7 shows a second embodiment of the connector 119 of the present invention. In this embodiment, the connector 119 comprises a housing 149 having lower and upper ends 150 and 151, and a central bore 153. The lower end 150 of the housing 149 comprises the connection compartment 154 where the port 134 of the endoscope 120 is received so that the endoscope 120 can be connected to the connector 119. As in the previous embodiment, lateral openings 171 around the connection compartment 154 allow an outside fluid, such as a sterilizing solution in the tray 122 (See FIG. 1A), to enter into the connection compartment 154 so as to treat the outer surface 144 of the port 134. The upper end 151 of the housing 149 comprises a tubing connector 158 to connect the fluid source (not shown) to the connector 119.

The central bore 153 comprises a piston assembly 194 which is centered within the central bore 153. The piston assembly comprises a piston body 195 with an upper plate 196, a lower plate 198 and an inner bore 204. The inner bore 204 extends along the body 195 and between the upper aperture 208 defined by the upper plate 196 and the lower aperture 210 defined by the lower plate 198. A piston spring 202 is concentrically placed around the piston body 195 and in the spring housing 220. The inner bore 204 connects the upper portion 155 of the central bore 153 to the connection compartment 154 so that when the connector 119 is connected to the endoscope port 134 a fluid communication between the endoscope 120 and the fluid source (not shown) can be established. As shown in FIG. 7, as a departure from the first embodiment, the inner bore 204 does not contain a valve. The lower plate 198 of the piston body comprises the piston surface 132 to sealably contact with the sealing surface 140 of the port 134 when the piston body 195 is moved towards the sealing surface 140.

During the operation, the piston body 195 is moved by the flow rate of the fluid so that at a predetermined reduced flow rate the piston body remains at its initial position as in the manner shown in FIG. 7. At this reduced flow rate, the fluid flows through the inner bore 204 so as to clean and sterilize the sealing surface 140. However, as the flow rate of the fluid is increased toward a higher flow rate, the pressure over the piston body 195 and, hence, the compressive force over the spring 202 increases. As a result, at a predetermined higher flow rate, the piston body moves toward the port 134 (in the direction of arrow 233) to seal the connection between the port 134 and the connector 119, while still allowing fluid to flow through the inner bore 204. When the piston surface 132 seals the sealing surface 140, as in the manner described above, fluid from the fluid source flows into the endoscope 120. In this embodiment, the compressive force on the spring 202 determines the flow rate necessary to seal the port 134.

Figures 8, 9:
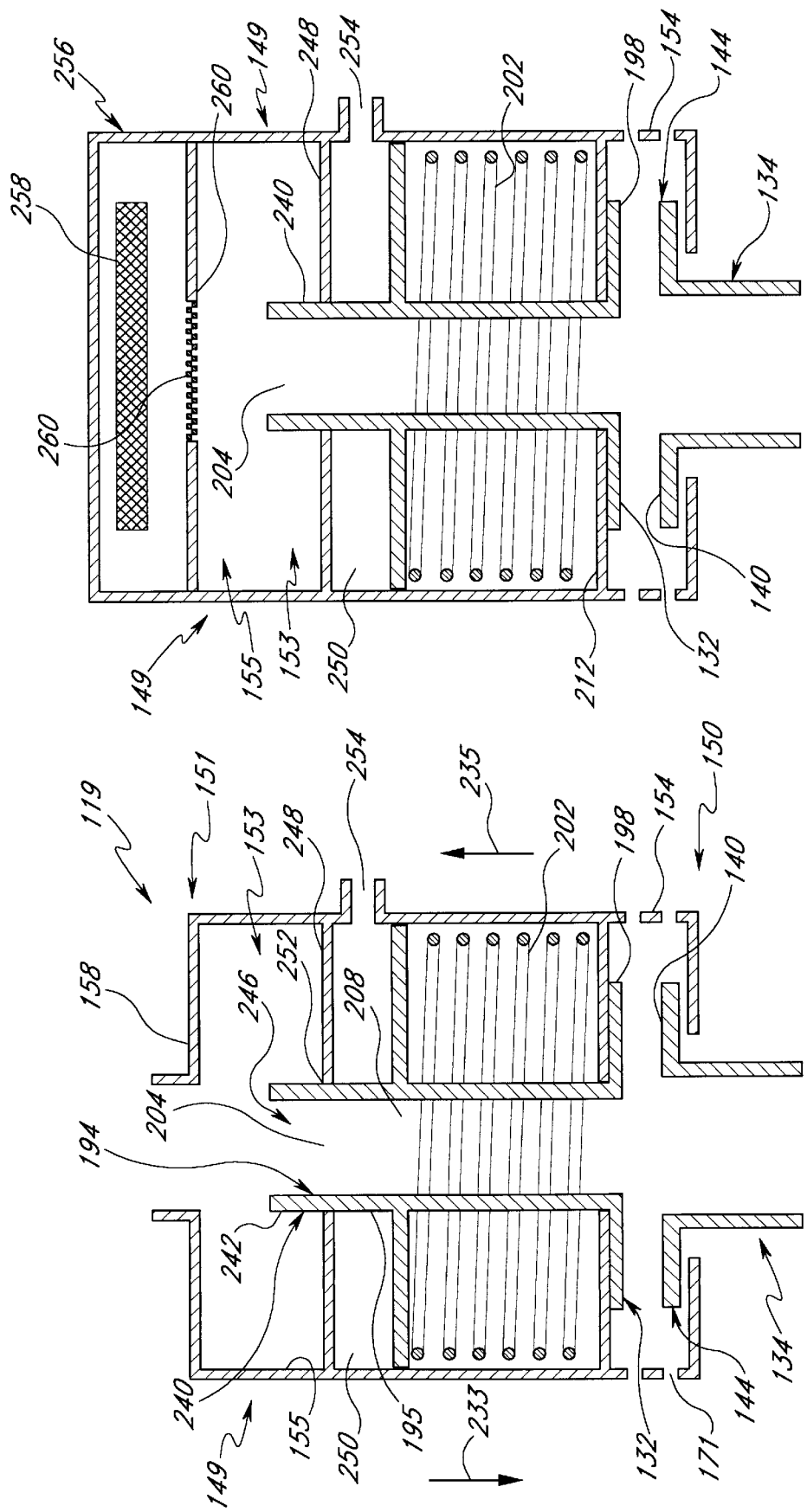

FIG. 8 shows a third embodiment of the connector 119 of the present invention. The connector 119 comprises a housing 149 having lower and upper ends 150 and 151, and a central bore 153. The lower end 150 of the housing 149 comprises the connection compartment 154 where the port 134 of the endoscope 120 is received so that the endoscope 120 can be connected to the connector 119. As in the previous embodiment, lateral openings 171 around the connection compartment 154 allow an outside fluid, such as a sterilizing solution in the tray 122 (See FIG. 1A), to enter into the connection compartment 154 so as to treat the outer surface 144 of the port. The upper end 151 of the housing 149 comprises a tubing connector 158 to connect the fluid source (not shown) to the connector 119.

In this embodiment, the central bore 153 comprises a piston assembly 194. As in the previous embodiments, the piston assembly 194 comprises a piston body 195 having an inner bore 204. However, in this embodiment, the piston body 195 may comprise an extension portion 242 attached to the piston body 195, as in the manner shown in FIG. 8. A side wall 244 of the extension portion 242 extends peripherally perpendicularly from an upper aperture 208 defined by an upper plate 196 of the piston body 195 (See, FIG. 7). In this configuration, the inner bore 204 may continuously extend from a lower aperture 210 defined by the lower plate 198 to an aperture 246 defined by the upper end of the side wall 242 of the extension portion 240. In this embodiment, the aperture 246 will be referred to as the upper aperture of the inner bore 204 hereafter. The lower plate 198 of the piston body comprises the piston surface 132 to sealably contact with the sealing surface 140 of the port 134 when the piston body 195 moves toward the sealing surface 140.

A piston spring 202 is concentrically placed around the piston body 195 and in the spring housing 220. The piston spring 202 biases the piston body 195 toward a second direction 235. In particular, in this embodiment, an annular plate 248 encloses a pressure chamber 250 above the upper plate 196. The pressure chamber can be alternatively placed under vacuum or pressure. As shown in FIG. 8, the annular plate 248 is placed about the extension portion 240 and is appropriately sized to permit the extension portion 240 to slip freely through the annular plate 248. A circumferential sealing edge 252 may be arranged on the annular plate and between the annular plate 248 and the extension portion 240 so as to provide a sealable contact between the annular plate 248 and the wall 242 of the extension portion 240. The annular plate 248 can be attached to the inner bore using suitable means, such as gluing, as in the manner shown in FIG. 8. A flow orifice 254 through the connector housing 149 connects the pressure chamber 250 to a fluid source. When the pressure chamber 250 is filled with a fluid from the fluid source (not shown), the pressure of the fluid urges the piston body in the first direction 233.

During the operation, the piston body 195 is moved by the fluid pressure in the pressure chamber 250. In this embodiment, at the beginning of the process, the fluid may be flown through the inner bore 204 so as to pretreat the outer surface 144 of the port 134. Since the port 134 is loosely connected to the connector 119, the fluid cleans and sterilizes the outer surface 144. The pressure in the pressure chamber is then increased to urge the piston toward the port 134 until the piston surface 132 comes in contact with the sealing surface 140 thereby sealing the connection between the connector 119 and the port 134. This allows sterilant fluid from the fluid source to flow into the endoscope 120. In this embodiment, upon completion of the process, the pressure in the chamber 250 is relieved which results in the piston body moving back as a result of the compressive force on the spring 202.

FIG. 9 illustrates a fourth embodiment of the connector 119. It will be appreciated that the connector 119 of this embodiment does not require an outside sterilant source. In particular, except for an enclosure 256, the rest of the connector 119 corresponds substantially to the embodiment illustrated in FIG. 8 and, therefore, the corresponding parts have the same reference numerals. Further, the foregoing description of the connector housing 149, the central bore 153, the piston assembly 194, the connection compartment 154 and the pressure chamber 250 is equally applicable to the fourth embodiment of the connector 119 shown in FIG. 9. In this embodiment, different from the previous embodiments, the housing 149 of the connector 119 comprises the enclosure 256 connected to the upper portion 155 of the central bore 153 thereby replacing the tubing connector 158 (See FIG. 8) used in the previous embodiments. In this embodiment, the enclosure 256 may contain a sterilant source 258, such as a container having a liquid sterilant, for example liquid hydrogen peroxide. A gas permeable membrane 260 separates the central bore 153 from the sterilant enclosure 256. The gas permeable membrane 260 may be made of a breathable membrane, such as porous PTFE, porous polyolefin, glass fiber or the like.

During the operation, the piston body 195 is moved by the fluid pressure in the pressure chamber 250. In this embodiment, at the beginning of the process, a sterilant fluid in the tray 122 (See FIG. 1A) may pretreat the outer surface 144 of the port 134. Since the port 134 is loosely connected to the connector 119, the sterilant fluid cleans and sterilizes the outer surface 144. However, as the pressure in the sterilization chamber 102 (See FIG. 1A) is reduced for a reduced pressure sterilization process, the liquid sterilant in the enclosure 256 evaporates which results in the sterilant vapor diffusing through the membrane 260 and subsequently passing through the inner bore 204 toward the port 134. This sterilant gas further sterilizes the outer surfaces 144 of the port 134 in reduced pressure. At this point, the pressure in the pressure chamber is increased to urge the piston toward the port 134 until the piston surface 132 comes in contact with the sealing surface 140 thereby sealing the connection between the connector 119 and the port 134. This allows sterilant gas from the enclosure 256 to flow into the endoscope 120. In this embodiment, upon completion of the process, the pressure in the chamber 250 is relieved which results in the piston body 195 moving back as a result of the compressive force on the spring 202.

FIG. 10 illustrates a fifth embodiment of the connector 119. As in the previous embodiment, the connector 119 of this embodiment does not require an outside sterilant source. The connector 119 illustrated in FIG. 10 corresponds to the fourth embodiment illustrated in FIG. 9 and in which corresponding parts have the same reference numerals. The description of the connector housing 149, the central bore 153, the piston body 195 and the connection compartment 154 is equally applicable to the sixth embodiment of the connector 119 shown in FIG. 10. However, in this embodiment, the sterilant enclosure 258 is formed as an integral part of the piston body 195 and is positioned on the upper aperture of the inner bore. The gas permeable membrane 260 at the upper aperture separates the inner bore of the piston body 195 from the enclosure 256. In this embodiment, the annular plate 248 is placed on the upper end of the central bore and encloses a pressure chamber 250 above the upper plate 196. As shown in FIG. 10, the annular plate 248 is placed about the extension portion 240 of the piston body 195 and is appropriately sized to permit the piston body 195 to slip freely through the annular plate 248. A circumferential sealing edge 252 may be arranged on the annular plate and between the annular plate 248 and the extension portion 240 so as to provide a sealable contact between the annular plate 248 and the wall 242 of the extension portion 240. In this embodiment, the spring 202 is located in the pressure chamber 250 between the upper plate 196 and the annular plate 248. Therefore, the locator ring 212 (See FIG. 9) that supported the spring 202 in the previous embodiments is no longer needed and, consequently, is removed. As shown in FIG. 10, it will be noted that, in this embodiment, the piston body 195 is biased against the connection member 170 of the connection compartment 154. As previously described, the connection member 170 of the connection compartment 154 engages with the port 134 when the port is connected to the connector 119.

In this embodiment, a check valve 264 is placed inside the pressure chamber 250 and preferably on the upper plate 196 as in the manner shown in FIG. 10. The check valve 264 communicates with the outside environment through a valve orifice 266 formed through the upper plate 196. The check valve 264 comprises a valve housing 268 having a valve member 270 and a spring 272. The spring 272 biases the valve member against a valve opening 274. When an outside gas pressure is lower than the pressure inside the pressure chamber 250, the valve member 270 overcomes the force of the spring 272 and the valve member 270 moves away from the valve opening 274 so that the pressure inside the chamber 250 is equalized with the outside environment pressure.

The operation of this embodiment will be explained with FIGS. 11 and 12. At the beginning of the process, the port 134 is connected to the connector 119. Due to the bias on the piston body, at this stage, the piston surface seals the sealing surface of the port and forms the aforementioned occluded areas. As the pressure in the sterilization chamber 102 (See FIG. 1A) is reduced for a reduced pressure sterilization process, the liquid sterilant in the enclosure 256 evaporates which results in the sterilant vapor diffusing through the membrane 260 and subsequently passing through the inner bore 204 toward the port 134. This sterilant gas flows into the endoscope 120. During the reduced pressure process, the valve 264 equalizes the pressure inside pressure chamber with the outside pressure so that the piston body 195 reseated on the port 134.

Figure 12:
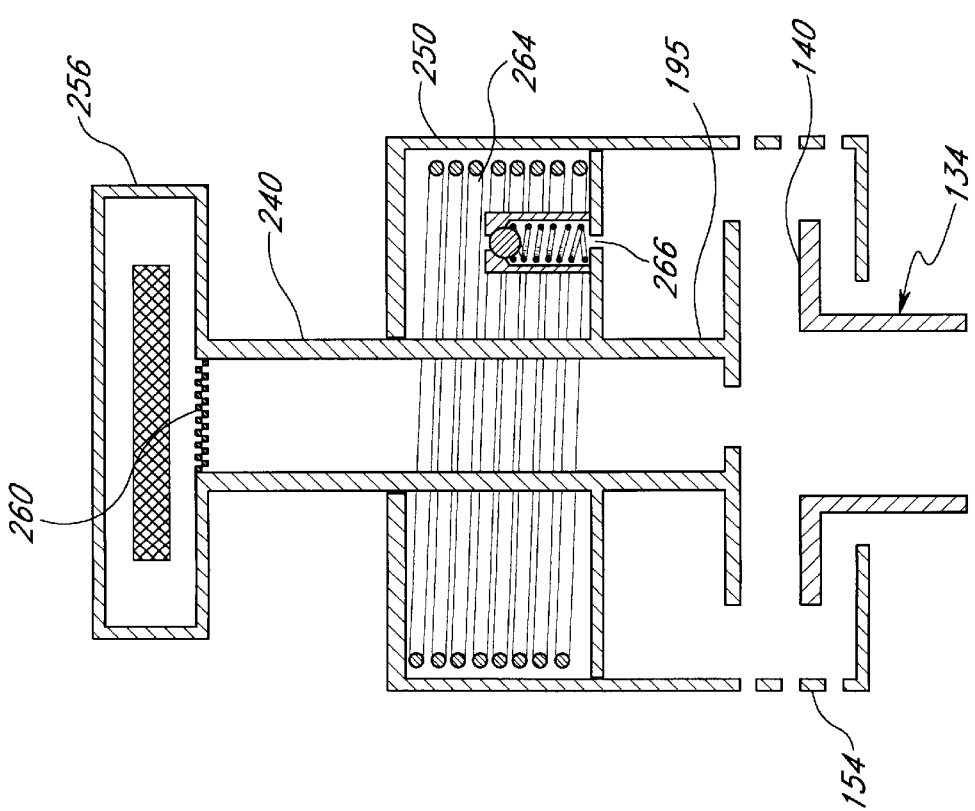

As shown in FIG. 12, when the pressure outside the connector is increased, the valve 264 keeps the pressure chamber 250 in reduced pressure which results in the piston body 195 moving upward and disconnecting with the port 134 thereby exposing the sealing surface of the port 134. Once the sealing surface (or any occlude portion of the outer surface 144 of the port) is exposed, the sealing surface can be sterilized using an outside sterilant injected into the sterilization chamber 102 (See FIG. 1A). The connector 119 of this embodiment is a single use device because the reduced pressure inside the pressure chamber cannot be increased. A final embodiment alleviates this situation.

Figure 13:
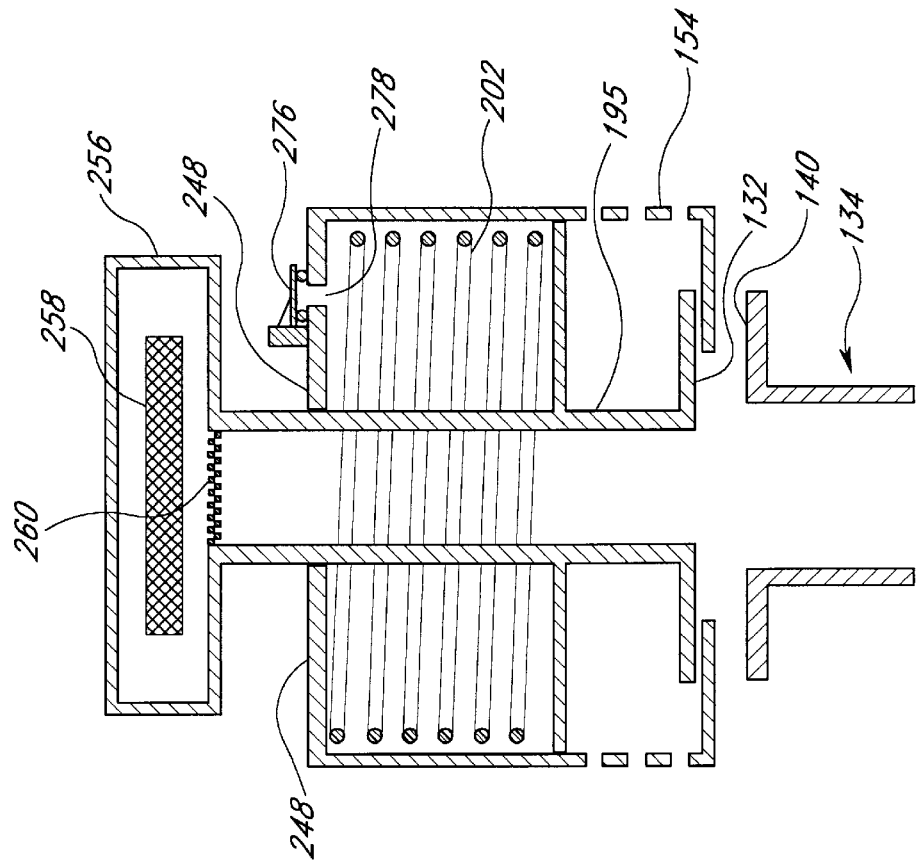
Figure 15:
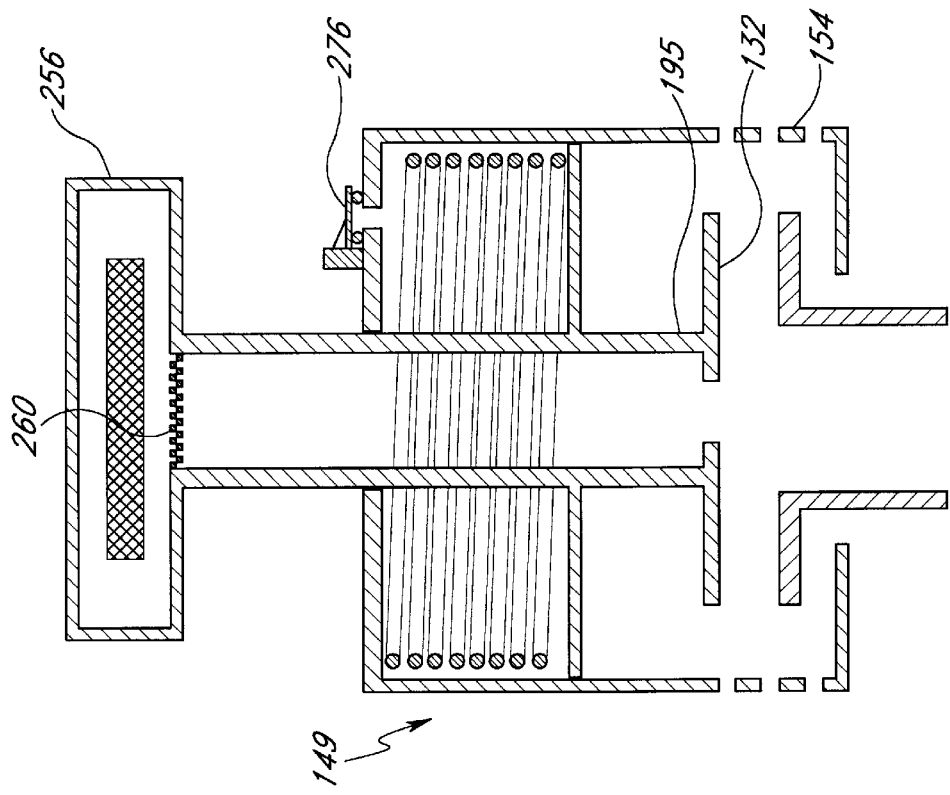
Figure 14:
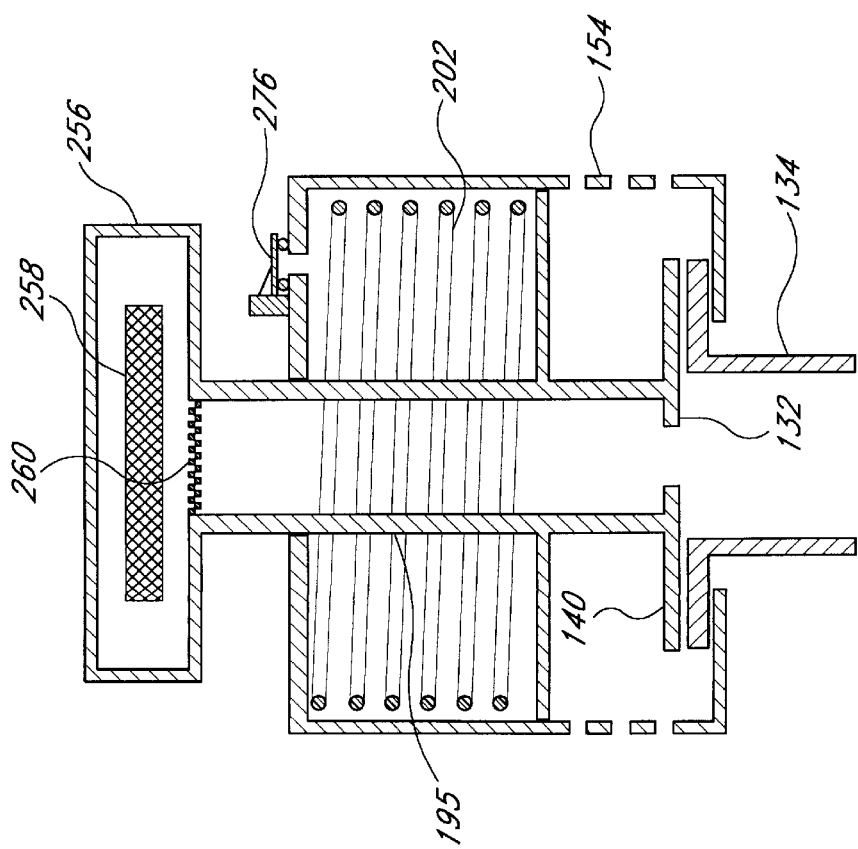

FIGS. 13–15 illustrate a seventh embodiment of the connector 119. As in the previous two embodiments, the connector 119 of this embodiment does not require an outside sterilant source. The connector 119 illustrated in FIG. 13 corresponds substantially to the sixth embodiment illustrated in FIGS. 10–12 and in which corresponding parts, therefore, have the same reference numerals. The description of the connector housing 149, the central bore 153, the piston body 195 and the connection compartment 154, the pressure chamber 250 and the sterilant enclosure 258 is equally applicable to the sixth embodiment of the connector 119 shown in FIGS. 13–15. However, in this embodiment, the check valve 264 illustrated therein is replaced in this embodiment by a pressure release cap 276. The pressure release cap 276 is placed on the pressure chamber 250 and preferably on the annular plate 248 as in the manner shown in FIG. 13. The pressure release cap 276 seals a pressure release orifice 278 formed through the annular plate 248. The pressure release cap 276 may have an o-ring to efficiently seal the orifice 278. A spring loaded hinge may be used to attach the cap 276 on the annular plate 248. The spring force biases the cap 276 toward the orifice 278 and seals the pressure chamber 250. As in the previous embodiment, when an outside gas pressure is lower than the pressure inside the pressure chamber 250, the pressure release cap 276 overcomes the spring force and opens the orifice 278 so that the pressure inside the chamber 250 is equalized with the outside environment pressure.

The function of the connector 119 of this embodiment likewise corresponds to that of the previous embodiments. As shown in FIG. 14, when the pressure outside the connector 119 is increased, the cap 276 keeps the pressure chamber 250 in reduced pressure which results in the piston body 195 moving upward and disconnecting with the port 134 thereby exposing the sealing surface of the port 134. Once the sealing surface (or any occlude portion of the outer surface 144 of the port) is exposed, the sealing surface can be sterilized using an outside sterilant injected into the sterilization chamber 102 (See FIG. 1A). As a departure from the previous embodiment, after this process the cap can be manually opened to release the low pressure. Therefore, the connector 119 of this embodiment is reusable.

Hence, although the foregoing description of the preferred embodiment of the present invention has shown, described and pointed out the fundamental novel features of the invention, it will be understood that various omissions, substitutions, and changes in the form of the detail of the apparatus and method as illustrated as well as the uses thereof, may be made by those skilled in the art, without departing from the spirit of the present invention. Consequently, the scope of the present invention should not be limited to the foregoing discussions, but should be defined by the appended claims.

What is claimed is:

1. A method for cleaning or sterilizing interior and exterior of a lumen device, said lumen device having a port that connected to the interior of the lumen device wherein the port has a sealing surface, the method comprising the steps of:

(a) connecting a connector device to the port, said connector having a housing and a pressure actuated member which is movably positioned within said housing, said pressure actuated member defines a passageway to allow fluid flow through the connector;

(b) placing said connector device and the lumen device in a chamber, wherein steps a and b can be performed in any order;

(c) positioning the pressure actuated member in a first position in which said connector is connected to the port and subjecting the lumen device to a fluid so that the fluid contacts the sealing surface of the port thereby treating the sealing surface with the fluid; and (d) positioning said pressure actuated member in a second position where a piston surface of said pressure actuated member fully engages with the sealing surface when said pressure actuated member is in said second position so as to induce said piston surface to seal with the sealing surface thereby allowing the fluid flowing into the interior of the lumen device, wherein steps (c) and (d) can be performed in either order.

2. The method of claim 1, wherein the step of connecting said connector device to the port comprises connecting to a connection compartment wherein said port is retained in said connection compartment by a locking member.

3. The method of claim 1, wherein the step of subjecting the lumen device to the fluid comprises subjecting said lumen device to a sterilant or cleaning solution.

4. The method of claim 1, wherein the step of positioning said pressure actuated member in a second position comprises allowing a sterilant or cleaning solution to flow into the interior of the lumen device.

5. The method of claim 1, wherein the step of positioning said pressure actuated member in a second position comprises increasing the pressure of said fluid flowing through said passageway so as to move said pressure actuated member from said first position to said second position.

6. The method of claim 1, wherein the step of positioning said pressure actuated member in a second position comprises using a pressurizing fluid, activating a solenoid, or activating a pneumatic device.

7. A method for sterilizing interior and exterior of a lumen device, said lumen device having a port that connected to the interior of the lumen device wherein the port has a sealing surface, the method comprising the steps of:

(a) connecting a connector device to the port and to a source of sterilant, said connector having a housing, and a pressure actuated member which is movably positioned within said housing, said pressure actuated member defines a passageway to allow sterilant flow through said connector;

(b) placing said connector devices and the lumen device in a sterilization chamber, wherein steps (a) and (b) can be performed in any order;

(c) positioning said pressure actuated member in a first position when said connector is connected to the port and subjecting the lumen device to a sterilant so that the sterilant contacts the sealing surface of the port thereby treating the sealing surface with the sterilant;

(d) subjecting the lumen device to reduced pressure; and (e) positioning said pressure actuated member in a second position, wherein a sterilant flows through said path way upon application of reduced pressure wherein a piston surface of said pressure actuated member fully engages with the sealing surface when said pressure actuated member is in said second position so as to induce said piston surface to seal with the sealing surface thereby allowing the sterilization fluid flowing through the path way to enter the interior of the lumen device, wherein steps c, d and e can be performed in any order.

8. The method of claim 7, wherein the step of connecting said connector device to the port comprises connecting to a connection compartment wherein said port is retained in said connection compartment by a locking member.

9. The method of claim 7, wherein the step of subjecting the lumen device to a sterilant comprises subjecting said lumen device to a liquid or vapor sterilant.

10. The method of claim 7, wherein the step of positioning said pressure actuated member comprises changing the pressure in said housing, activating a solenoid, or activating a pneumatic device.

* * * * *

UNITED STATES PATENT AND TRADEMARK OFFICE
CERTIFICATE OF CORRECTION

PATENT NO.    : 6,041,794                                                                  Page 1 of 1
DATED         : March 28, 2000
INVENTOR(S)   : Szu-Min Lin, Paul T. Jacobs, Paul Leonard, Rodrigo Berho, Douglas W. Fett and
                Keith Schubert It is certified that error appears in the above-identified patent and that said Letters Patent is hereby corrected as shown below:

Column 13,
Lines 40-41, please delete the phrase "port that connected" and replace it with the phrase -- port connected --.

Column 14,
Line 22, please delete the phrase "port that connected" and replace it with the phrase -- port connected --.

Signed and Sealed this

Twenty-ninth Day of October, 2002

Attest:

Attesting Officer

JAMES E. ROGAN
Director of the United States Patent and Trademark Office